(12) United States Patent
Briggs et al.

(10) Patent No.: US 9,402,796 B2
(45) Date of Patent: Aug. 2, 2016

(54) KIT COMPRISING A HAIR CONDITIONING COMPOSITION AND AN ACTIVATOR COMPOSITION

(71) Applicant: Conopco, Inc., Englewood Cliffs, NJ (US)

(72) Inventors: Stephen Leonard Briggs, Bromborough (GB); Andrew Tattersall, Liverpool (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/404,656

(22) PCT Filed: May 24, 2013

(86) PCT No.: PCT/EP2013/060797
§ 371 (c)(1),
(2) Date: Dec. 1, 2014

(87) PCT Pub. No.: WO2013/178556
PCT Pub. Date: Dec. 5, 2013

(65) Prior Publication Data
US 2015/0157544 A1    Jun. 11, 2015

(30) Foreign Application Priority Data
Jun. 1, 2012   (EP) .................................... 12170617

(51) Int. Cl.
| | | |
|---|---|---|
| *A61Q 5/00* | (2006.01) | |
| *A61Q 5/12* | (2006.01) | |
| *A61K 8/34* | (2006.01) | |
| *A61K 8/41* | (2006.01) | |
| *A61K 8/39* | (2006.01) | |
| *A61K 8/02* | (2006.01) | |

(52) U.S. Cl.
CPC .............. *A61K 8/416* (2013.01); *A61K 8/0295* (2013.01); *A61K 8/342* (2013.01); *A61K 8/39* (2013.01); *A61Q 5/12* (2013.01); *A61K 2800/48* (2013.01); *A61K 2800/882* (2013.01); *A61K 2800/884* (2013.01)

(58) Field of Classification Search
None
See application file for complete search history.

(56) References Cited

U.S. PATENT DOCUMENTS

| | | | | |
|---|---|---|---|---|
| 5,538,720 | A * | 7/1996 | Jendryssek-Pfaff | ..... A61K 8/20 424/70.1 |
| 5,972,322 | A | 10/1999 | Rath et al. | |
| 2001/0016201 | A1* | 8/2001 | Janchitraponvej | ............ 424/400 |
| 2003/0059377 | A1* | 3/2003 | Riley | ..................... A61K 8/046 424/47 |
| 2003/0108502 | A1* | 6/2003 | Uchida | .................... A61K 8/19 424/70.11 |

FOREIGN PATENT DOCUMENTS

| | | |
|---|---|---|
| EP | 0586929 | 3/1994 |
| EP | 1393715 | 3/2004 |
| EP | 1393715 A1 | 3/2004 |
| EP | 2196178 A1 | 6/2010 |
| WO | WO 0000170 A1 * | 1/2000 |
| WO | WO0219977 | 3/2002 |
| WO | WO02096381 | 12/2002 |
| WO | WO2006118942 | 11/2006 |
| WO | WO2013037750 A1 | 3/2013 |

OTHER PUBLICATIONS

IPRP2 in PCTEP2013060797 dated Sep. 29, 2014; p. 1 to p. 15.
Search Report in EP12170617 dated Feb. 22, 2013; p. 16 to p. 20.
Search Report in PCTEP2013060797 dated Apr. 22, 2014; p. 21 to p. 24.
Written Opinion in EP12170617 dated Feb. 22, 2013; p. 25 to p. 25 to p. 32.
Written Opinion in PCTEP2013060797 dated Apr. 22, 2014; p. 33 to p. 43.

* cited by examiner

*Primary Examiner* — Tracy Vivlemore
*Assistant Examiner* — Monica Shin
(74) *Attorney, Agent, or Firm* — Greenberg Traurig, LLP

(57) ABSTRACT

Kit comprising an aqueous hair conditioning composition comprising a cationic surfactant and fatty alcohol, and an anhydrous activator composition which comprises polyalkylene glycol. Method of treating the hair comprising applying an activator composition to a hair conditioning composition, mixing, and then applying to the hair. Method of treating the hair comprising applying a hair conditioning composition to the hair and then applying an activator composition to the hair. Method of texturising a hair conditioning composition by mixing with an activator composition.

2 Claims, No Drawings

KIT COMPRISING A HAIR CONDITIONING COMPOSITION AND AN ACTIVATOR COMPOSITION

The present invention relates to a kit for treating the hair.

EP-A-1 393 715 (Beiersdorf) discloses a kit comprising a shampoo and a heat activator composition.

EP-A-0 586 929 (Kao) discloses a conditioning composition with polyethylene glycol and a separate heat activating composition.

WO 02/19977 (P&G) discloses a variety of hair treatment compositions which are mixed with a heat activating component.

Despite the prior art there remains a need for improved hair conditioning compositions.

Accordingly, and in a first aspect there is provided a kit according to claim 1.

The cationic surfactant and fatty alcohol combine to form a conditioning gel phase in lamellar form. This is necessary to exhibit the viscosity modification when mixed with the activator composition.

Raising the viscosity of a hair conditioning composition results in a product with a more luxurious sensory appeal and a creamy rich texture. These are considered to be desirable attributes to the consumer.

Preferably, the volume of the hair conditioning composition is greater than that of the activator composition. More preferably, the ratio between the hair conditioning composition and the activator composition is from 1.5:1 to 10:1.

Preferably, the activator composition is from 5 to 15 ml. Preferably, the hair conditioning composition is from 6 to 50 ml.

Preferably the polyalkylene glycol has a molecular weight of above 100, more preferably 150 and especially preferably above 300. Preferably, the polyalkylene glycol has a molecular weight below 1 000, more preferably 750, and especially preferably 600.

Preferably, the polyalkylene glycol is polyethylene glycol (PEG), and more preferably is PEG 200 or PEG 400. Most preferably it is PEG 400.

Preferably, the kit comprises a multi-compartment package for the hair treatment composition and the activator composition which are maintained separate from one another prior to dispensing. Preferably, the hair conditioning composition and the activator composition are dispensed simultaneously. This permits the two components to be mixed more easily by the consumer immediately prior to use. The multi-compartment package can be a tube or a pump action package. Preferably, the dual compartment package comprises means for contacting the two compositions prior to applying to the hair.

Preferably, the package comprises means for dispensing the two compositions either individually or as a mixture of the two.

In a second aspect there is provided a method of treating the hair comprising applying an activator composition to a hair conditioning composition, mixing, and then applying to the hair.

In a third aspect there is provided a method of treating the hair comprising applying a hair conditioning composition to the hair and then applying an activator composition to the hair.

In a fourth aspect there is provided a method of modifying the texture and consumer relevant sensorial attributes of a hair conditioning composition by mixing with an activator composition.

The activator composition is preferably an anhydrous composition comprising from 90 to 100% wt. polyalkylene glycol, more preferably 99-100% wt. polyalkylene glycol.

The anhydrous activator composition preferably comprises substantially no water. By substantially no water is meant less than 0.5% wt. water.

The hair conditioning composition may be any of the dedicated conditioning composition formats such as rinse-off conditioner, leave-one conditioner, mask, etc.

Preferably, the conditioning composition comprises a cationic surfactant, used singly or in admixture. Examples include quaternary ammonium hydroxides or salts thereof, e.g. chlorides.

Suitable conditioning surfactants include those selected from cationic surfactants, used singly or in admixture. Preferably, the cationic surfactants have the formula $N^+R^1R^2R^3R^4$ wherein $R^1$, $R^2$, $R^3$ and $R^4$ are independently ($C_1$ to $C_{30}$) alkyl or benzyl. Preferably, one, two or three of $R^1$, $R^2$, $R^3$ and $R^4$ are independently ($C_4$ to $C_{30}$) alkyl and the other $R^1$, $R^2$, $R^3$ and $R^4$ group or groups are ($C_1$-$C_6$) alkyl or benzyl. More preferably, one or two of $R^1$, $R^2$, $R^3$ and $R^4$ are independently ($C_6$ to $C_{30}$) alkyl and the other $R^1$, $R^2$, $R^3$ and $R^4$ groups are ($C_1$-$C_6$) alkyl or benzyl groups. Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (eg, oleyl). Alkyl groups are optionally ethoxylated on the alkyl chain with one or more ethyleneoxy groups.

Suitable cationic surfactants for use in conditioner compositions according to the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (eg, Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant.

Another example of a class of suitable cationic surfactants for use in the invention, either alone or together with one or more other cationic surfactants, is a combination of (i) and (ii) below:

(i) an amidoamine corresponding to the general formula (I):

$$R1CONH(CH2)mN(R2)R3 \quad (I)$$

in which $R^1$ is a hydrocarbyl chain having 10 or more carbon atoms, $R^2$ and $R^3$ are independently selected from hydrocarbyl chains of from 1 to 10 carbon atoms, and m is an integer from 1 to about 10; and (ii) an acid.

As used herein, the term hydrocarbyl chain means an alkyl or alkenyl chain.

Preferred amidoamine compounds are those corresponding to formula (I) in which $R^1$ is a hydrocarbyl residue having from about 11 to about 24 carbon atoms, $R^2$ and $R^3$ are each independently hydrocarbyl residues, preferably alkyl groups, having from 1 to about 4 carbon atoms, and m is an integer from 1 to about 4.

Preferably, $R^2$ and $R^3$ are methyl or ethyl groups.

Preferably, m is 2 or 3, i.e. an ethylene or propylene group.

Preferred amidoamines useful herein include stearamidopropyldimethylamine, stearamidopropyldiethylamine, stearamidoethyldiethylamine, stearamidoethyldimethylamine, palmitamidopropyldimethylamine, palmitamidopropyl-diethylamine, palmitamidoethyldiethylamine, palmitamidoethyldimethylamine, behenamidopropyldimethylamine, behenamidopropyldiethylmine, behenamidoethyldiethyl-amine, behenamidoethyldimethylamine, arachidamidopropyl-dimethylamine, arachidamidopropyldiethylamine, arachid-amidoethyldiethylamine, arachidamidoethyldimethylamine, and mixtures thereof.

Particularly preferred amidoamines useful herein are stearamidopropyldimethylamine, stearamidoethyldiethylamine, and mixtures thereof.

Commercially available amidoamines useful herein include: stearamidopropyldimethylamine with tradenames LEXAMINE S-13 available from Inolex (Philadelphia Pa., USA) and AMIDOAMINE MSP available from Nikko (Tokyo, Japan), stearamidoethyldiethylamine with a tradename AMIDOAMINE S available from Nikko, behenamidopropyldimethylamine with a tradename INCROMINE BB available from Croda (North Humberside, England), and various amidoamines with tradenames SCHERCODINE series available from Scher (Clifton N.J., USA).

A protonating acid may be present. Acid may be any organic or mineral acid which is capable of protonating the amidoamine in the conditioner composition. Suitable acids useful herein include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, lactic acid and mixtures thereof.

The primary role of the acid is to protonate the amidoamine in the hair treatment composition thus forming a tertiary amine salt (TAS) in situ in the hair treatment composition. The TAS in effect is a non-permanent quaternary ammonium or pseudo-quaternary ammonium cationic surfactant.

Suitably, the acid is included in a sufficient amount to protonate more than 95 mole % (293 K) of the amidoamine present.

In conditioners of the invention, the level of cationic surfactant will generally range from 0.01% to 10%, more preferably 0.05% to 7.5%, most preferably 0.1% to 5% by weight of the composition.

Preferably, the conditioning composition of the invention contains emulsified droplets of a silicone conditioning agent.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188.

The viscosity of the emulsified silicone itself (not the emulsion or the final hair conditioning composition) is typically at least 10,000 cst at 25° C. the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in the shampoo compositions of the invention will typically have an average silicone droplet size in the composition of less than 30, preferably less than 20, more preferably less than 10 micron, ideally from 0.01 to 1 micron. Silicone emulsions having an average silicone droplet size of £ 0.15 micron are generally termed microemulsions.

Emulsified silicones for use in the conditioner compositions of the invention will typically have an size in the composition of less than 30, preferably less than 20, more preferably less than 15. Preferably the average silicone droplet is greater than 0.5 micron, more preferably greater than 1 micron, ideally from 2 to 8 micron.

Silicone particle size may be measured by means of a laser light scattering technique, for example using a 2600D Particle Sizer from Malvern Instruments.

Examples of suitable pre-formed emulsions include Xiameter MEM 1785 and microemulsion DC2-1865 available from Dow Corning. These are emulsions/microemulsions of dimethiconol. Cross-linked silicone gums are also available in a pre-emulsified form, which is advantageous for ease of formulation.

A further preferred class of silicones for inclusion in shampoos and conditioners of the invention are amino functional silicones. By "amino functional silicone" is meant a silicone containing at least one primary, secondary or tertiary amine group, or a quaternary ammonium group. Examples of suitable amino functional silicones include: polysiloxanes having the CTFA designation "amodimethicone".

Specific examples of amino functional silicones suitable for use in the invention are the aminosilicone oils DC2-8220, DC2-8166 and DC2-8566 (all ex Dow Corning).

Suitable quaternary silicone polymers are described in EP-A-0 530 974. A preferred quaternary silicone polymer is K3474, ex Goldschmidt.

Also suitable are emulsions of amino functional silicone oils with non ionic and/or cationic surfactant.

Pre-formed emulsions of amino functional silicone are also available from suppliers of silicone oils such as Dow Corning and General Electric. Specific examples include DC939 Cationic Emulsion and the non-ionic emulsions DC2-7224, DC2-8467, DC2-8177 and DC2-8154 (all ex Dow Corning).

The total amount of silicone is preferably from 0.01 wt % to 10% wt of the total composition more preferably from 0.1 wt % to 5 wt %, most preferably 0.5 wt % to 3 wt % is a suitable level.

Compositions according to the present invention may also comprise a dispersed, non-volatile, water-insoluble oily conditioning agent. Preferably such non-silicone conditioning oily conditioning agents are present in conditioner compositions.

By "insoluble" is meant that the material is not soluble in water (distilled or equivalent) at a concentration of 0.1% (w/w), at 25° C.

Suitable oily or fatty materials are selected from hydrocarbon oils, fatty esters and mixtures thereof. Straight chain hydrocarbon oils will preferably contain from about 12 to about 30 carbon atoms. Also suitable are polymeric hydrocarbons of alkenyl monomers, such as $C_2$-$C_6$ alkenyl monomers.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used.

Suitable fatty esters are characterised by having at least 10 carbon atoms, and include esters with hydrocarbyl chains derived from fatty acids or alcohols, Monocarboxylic acid esters include esters of alcohols and/or acids of the formula R'COOR in which R' and R independently denote alkyl or alkenyl radicals and the sum of carbon atoms in R' and R is at least 10, preferably at least 20. Di- and trialkyl and alkenyl esters of carboxylic acids can also be used.

Particularly preferred fatty esters are mono-, di- and triglycerides, more specifically the mono-, di-, and tri-esters of glycerol and long chain carboxylic acids such as $C_1$-$C_{22}$ carboxylic acids. Preferred materials include cocoa butter, palm stearin, sunflower oil, soyabean oil and coconut oil.

The oily or fatty material is suitably present at a level of from 0.05 wt % to 10 wt %, preferably from 0.2 wt % to 5 wt %, more preferably from about 0.5 wt % to 3 wt %.

Such conditioner compositions will typically comprise one or more conditioning surfactants which are cosmetically acceptable and suitable for topical application to the hair.

Conditioners of the invention will typically also incorporate a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 22. Fatty alcohols are typically compounds containing straight chain alkyl groups. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention will generally range from 0.01 to 10%, preferably from 0.1% to 8%, more preferably from 0.2% to 7%, most preferably from 0.3% to 6% by weight of the composition. The weight ratio of cationic surfactant to fatty alcohol is suitably from 1:1 to 1:10, preferably from 1:1.5 to 1:8, optimally from 1:2 to 1:5. If the weight ratio of cationic surfactant to fatty alcohol is too high, this can lead to eye irritancy from the composition. If it is too low, it can make the hair feel squeaky for some consumers.

Embodiments will now be described in the following non-limiting examples.

EXAMPLE 1

Test Formulation 1

| Ingredient | % in composition |
|---|---|
| Water | 75.078 |
| Buffer (88%) | 1.000 |
| Behentrimonium chloride (70%) | 1.500 |
| Stearamidopropyl Dimethylamine | 1.500 |
| Cetearyl alcohol 30/70 | 4.000 |
| Paraffin Wax 125 | 1.000 |
| Glycerol | 3.000 |

-continued

| Ingredient | % in composition |
|---|---|
| Amodimethicone | 1.000 |
| Amodimethicone (70%) | 4.286 |
| PEG 150/stearyl alcohol/SMDI copolymer | 1.000 |
| PEG 180M | 0.0100 |
| Preservative | 1.0000 |
| EDTA | 0.100 |
| Preservative | 0.060 |
| Fragrance | 0.500 |
| 30% L-Lysene (30%) | 3.333 |

Test Formulation 2

| Ingredient | Wt. % active level |
|---|---|
| Cetearyl alcohol | 5.00 |
| TAS | 1.25 |
| BTAC | 0.86 |
| Mineral Oil | 0.2 |
| Petrolatum | 0.1 |
| PEG | 0.01 |
| Aminosilicone | 1.00 |
| Lactic Acid | 0.9 |
| Preservative | 0.6 |
| Buffer | 0.25 |
| Glycerin | 0.2 |
| Water | To 100 |

Activator Composition

PEG-8

EXAMPLE 2

The table shows the viscosity increase caused by the activator composition. The comparative shows that the viscosity increasing effect is limited to conditioner compositions.

Viscosity is measured at 30° C. and at atmospheric pressure.

| Test:Activator | | PEG 400 | | PEG 200 | |
|---|---|---|---|---|---|
| | (v:v) | T bar B | RV5 | T bar B | RV5 |
| Test 1 (CN) | No activator | 237 000 | 9 980 | — | — |
| | 1:1 | 15 200 | 1 700 | — | — |
| | 2:1 | 318 000 | 13 060 | — | — |
| | 3:1 | 284 000 | 16 620 | — | — |
| Test 2 (LA) | No activator | 114 000 | 7 880 | 114 000 | 7 880 |
| | 1:1 | 46 400 | 2 780 | | |
| | 2:1 | 357 000 | 15 500 | 312 000 | 13 100 |
| | 3:1 | 261 000 | 12 660 | 256 000 | 11 640 |
| | 4:1 | 316 000 | 12 780 | — | — |
| | 5:1 | 265 000 | 12 080 | — | — |
| Comparative A (SH) | No activator | 5 280 | — | — | — |
| | 2:1 | 0 | — | — | — |
| | 3:1 | 0 | — | — | — |

The data shows:

Viscosity increases when more than 1:1 (v:v) activator is used the viscosity of the product increases over the base level.

Viscosity increase is seen with PEG 200 and PEG 400.

Viscosity increase is not seen in shampoo formulation. In fact the viscosity drops to practically zero.

The invention claimed is:

1. Kit comprising
an aqueous hair conditioning composition comprising a cationic surfactant and fatty alcohol, and
an anhydrous activator composition consisting of polyalkylene glycol
wherein the polyalkylene glycol is polyethylene glycol (PEG);
wherein the polyethylene glycol (PEG) has a molecular weight of 100 to 1000;
wherein the aqueous hair conditioning composition and the polyethylene glycol (PEG) are present in a volumetric ratio of 2:1 to 5:1; and
wherein the kit further comprises a dual compartment package for the hair conditioning composition and the activator composition which are maintained separate from one another.

2. Method of treating the hair comprising combining an anhydrous activator composition consisting of polyalkylene glycol, to an aqueous hair conditioning composition comprising a cationic surfactant and fatty alcohol, mixing, and then applying to the hair;
wherein the polyalkylene glycol is polyethylene glycol (PEG);
wherein the polyethylene glycol (PEG) has a molecular weight of 100 to 1000;
wherein the aqueous hair conditioning composition and the polyethylene glycol (PEG) are present in a volumetric ratio of 2:1 to 5:1.

* * * * *